(12) United States Patent
Qiu et al.

(10) Patent No.: US 6,410,766 B2
(45) Date of Patent: Jun. 25, 2002

(54) EMITTING MATERIALS USED FOR ORGANIC EL BASED ON TRIDENTATE LIGANDS

(75) Inventors: Yong Qiu; Yan Shao, both of Beijing (CN)

(73) Assignee: Tsinghau University, Beijing (CN)

( * ) Notice: Subject to any disclaimer, the term of this patent is extended or adjusted under 35 U.S.C. 154(b) by 0 days.

(21) Appl. No.: 09/755,688

(22) Filed: Jan. 5, 2001

(30) Foreign Application Priority Data

Jan. 7, 2000 (CN) ........................................ 00100040 A

(51) Int. Cl.$^7$ .................................................. C07F 5/06
(52) U.S. Cl. .................... 556/33; 556/182; 534/613; 252/301.18
(58) Field of Search ..................... 556/33, 182; 534/613; 252/301.18

(56) References Cited

U.S. PATENT DOCUMENTS

| | | | |
|---|---|---|---|
| 4,178,382 A | * 12/1979 | Mao et al. | 556/182 X |
| 4,655,785 A | * 4/1987 | Reinert et al. | 556/33 X |
| 4,720,432 A | 1/1988 | VanSlyke et al. | 428/457 |
| 5,141,671 A | 8/1992 | Bryan et al. | 252/301.16 |
| 5,917,073 A | * 6/1999 | Kondoh et al. | 556/182 X |
| 5,925,777 A | * 7/1999 | Harada et al. | 556/182 X |

OTHER PUBLICATIONS

Diehl et al., "Fluorometric and Spectrophotometric Determination of Magnesium with o,o'–Dihydroxyazobenzene", Analytical Chemistry 35:1144–1154, 1963.

Shen et al., "Three Color, Tunable, Organic Light–Emitting Devices", Science 276:2009–2011, 1997.

Tang et al, "Organic Electroluminescent Diodes", Appl. Phys. Lett. 51:913–915, 1987.

* cited by examiner

Primary Examiner—Paul F. Shaver
(74) Attorney, Agent, or Firm—Fish & Richardson P.C.

(57) ABSTRACT

A series of emitting materials used for organic EL based on tridentate ligands are characterized as Formula 1, Formula 2 and Formula 3, where: the group O-I-N is a bidentate ligand such as 8-hydroxyquinoline and 2-(o-hydroxyphenyl)-benzoxazole, II, III are unsubstituted or substituted aryl groups. The substituted groups can have 1–8 carbon atoms, halogen, cyano, amino, amido, sulfonyl, carbonyl, aryl, or heteroalkyl groups. The ligand including II and III is a tridentate ligand with three chelate atoms: two oxygen atoms and one nitrogen atom. The central metal atoms can be trivalent or tetravalent atoms such as Al, In, Ga, Tl, and Sn. These materials can be used as emitting materials or electronic transport materials in organic EL devices.

Formula 1

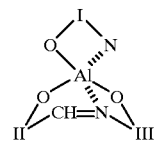

Formula 2

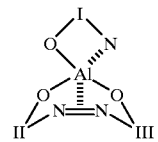

Formula 3

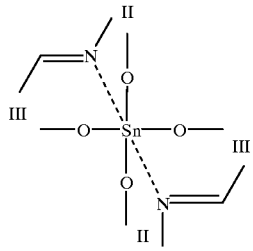

11 Claims, 8 Drawing Sheets

FIG. 4

ATOMIC COMPOSITION REPORT (MANUAL)

SELECTED ISOTOPES:

| SYMBOL | MIN | MAX | V'CY | NAME |
|---|---|---|---|---|
| C | 0 | 30 | 4 | CARBON-12 |
| H | 0 | 50 | 1 | HYDROGEN-1 |
| O | 0 | 5 | 2 | OXYGEN-16 |
| N | 0 | AUTO | 3 | NITROGEN-14 |
| Al | 1 | 2 | 3 | ALUMINIUM-27 |

ALLOWABLE ERROR = MINIMUM OF 5.0 PPM, 10.0 MMU.
RING/DOUBLE BOND LIMITS = (−0.5:40.0)

| MASS | CALCULATED | ppm | mmu | R/DB | FORMULA |
|---|---|---|---|---|---|
| 382.08793 | 382.08763 | −0.8 | −0.3 | 11.0 | $C_3H_7O_2N_{20}Al$ |
|  | 382.08828 | 0.9 | 0.4 | 20.0 | $C_{26}H_{16}Al_2$ |
|  | 382.08745 | −1.3 | −0.5 | 8.0 | $C_{10}H_{16}O_5N_8Al_2$ |
|  | 382.08744 | −1.3 | −0.5 | 13.5 | $C_9H_{10}N_{15}Al_2$ |
|  | 382.08847 | 1.4 | 0.5 | 17.5 | $C_{20}H_{13}O_2N_5Al$ |
|  | 382.08712 | −2.1 | −0.8 | 18.0 | $C_{18}H_{11}ON_8Al$ |
|  | 382.08879 | 2.2 | 0.9 | 13.0 | $C_{11}H_{12}ON_{12}Al_2$ |
|  | 382.08897 | 2.7 | 1.0 | 10.5 | $C_5H_9O_3N_{17}Al$ |
|  | 382.08628 | −4.3 | −1.6 | 11.5 | $CH_5ON_{23}Al$ |
|  | 382.08611 | −4.8 | −1.8 | 8.5 | $C_8H_{14}O_4N_{11}Al_2$ |
|  | 382.08981 | 4.9 | 1.9 | 17.0 | $C_{22}H_{15}O_3N_2Al$ ← |

FIG. 6

```
ION MASS = 383.0845240

CHARGE = +1
TOLERANCE = 0.0100000

DBE MIN = -2
DBE MAX = 200

MAX CANDIDATES = 10
```

| ATOM | #(MIN, | MAX) | WT%(MIN, | MAX) |
|------|--------|------|----------|--------|
| C    | 10     | 25   | 0.00     | 100.00 |
| H    | 10     | 45   | 0.00     | 100.00 |
| O    | 0      | 5    | 0.00     | 100.00 |
| N    | 0      | 5    | 0.00     | 100.00 |
| 27Al | 0      | 2    | 0.00     | 100.00 |

| # | C | H | O | N | 27Al | MASS | ERROR |
|---|---|---|---|---|------|------|-------|
| *** MASS ANALYSIS FOR MASS 383.0845240 | | | | | | | |
| 1 | 21 | 14 | 3 | 3 | 1 | 383.0845062 | 4.649e-08 |
| 2 | 23 | 16 | 4 | 0 | 1 | 383.0858489 | 3.458e-06 |
| 3 | 25 | 15 | 0 | 1 | 2 | 383.0829778 | 4.036e-06 |
| 4 | 24 | 12 | 0 | 4 | 1 | 383.0871863 | 6.950e-06 |
| 5 | 16 | 17 | 4 | 4 | 2 | 383.0875084 | 7.790e-06 |
| 6 | 16 | 14 | 5 | 5 | 1 | 383.0804834 | 1.055e-05 |
| 7 | 22 | 17 | 3 | 0 | 2 | 383.0802977 | 1.103e-05 |
| 8 | 18 | 19 | 5 | 1 | 2 | 383.0888510 | 1.130e-05 |

EMITTING MATERIALS USED FOR ORGANIC EL BASED ON TRIDENTATE LIGANDS

BACKGROUND OF THE INVENTION

This invention relates to novel emitting materials for organic electroluminescence (EL) devices. As a promising technology for flat panel display, organic EL has attracted more and more attentions. The early efficient devices have been reported in C. W. Tang, S. A. Van Slyke, Appl. Phys. Lett. 1987, 51:913~915 and U.S. Pat. No. 4,720,432 issued Jan. 19, 1988. Great improvements have been made since 1987 and many new materials have been synthesized and used in organic EL devices. There are diverse emitting materials used in fabrication of organic EL devices with blue, green, yellow, and red emission.

SUMMARY OF THE INVENTION

The primary object of this invention is provide to a series of stable complexes based on many kinds of tridentate ligands. These materials exhibited strong fluorescence and excellent amorphous properties in solid state. Both of these characters are conducive to forming high quality amorphous films.

Another object of the invention is provide to the use of such novel complexes as thermal stable emitting materials for organic light-emitting diodes (OLEDs).

This invention disclosed here a series of stable complexes which have a tridentate ligand. Almost all of these complexes have the high Tg more than 200° C. The advantage of these materials lies in their excellent thermal stability and good performance to form amorphous films. The materials in this invention have made some progress in improving the compatibility with other layers materials. These materials have some unique characteristics that will be conducive to forming high quality amorphous films. Such novel complexes can be used as a thermal stable emitting material for OLEDs. In addition, a series of emitting colors have bene obtained from these materials including green, yellow, and red, some of which are remain rare now. And the color position in the color coordinates system shows strong potential as a red light-emitting material for organic electroluminescence. These materials can be used as emitting materials or electronic transport materials in organic EL devices.

BRIEF DESCRIPTION OF THE DRAWINGS

FIG. 4 is the computer search result of the high-resolution mass spectrum of Complex 1.

FIG. 6 is the computer search result of the high-resolution mass spectrum of Complex 12.

DETAILED DESCRIPTION OF THE INVENTION

Figure 1:
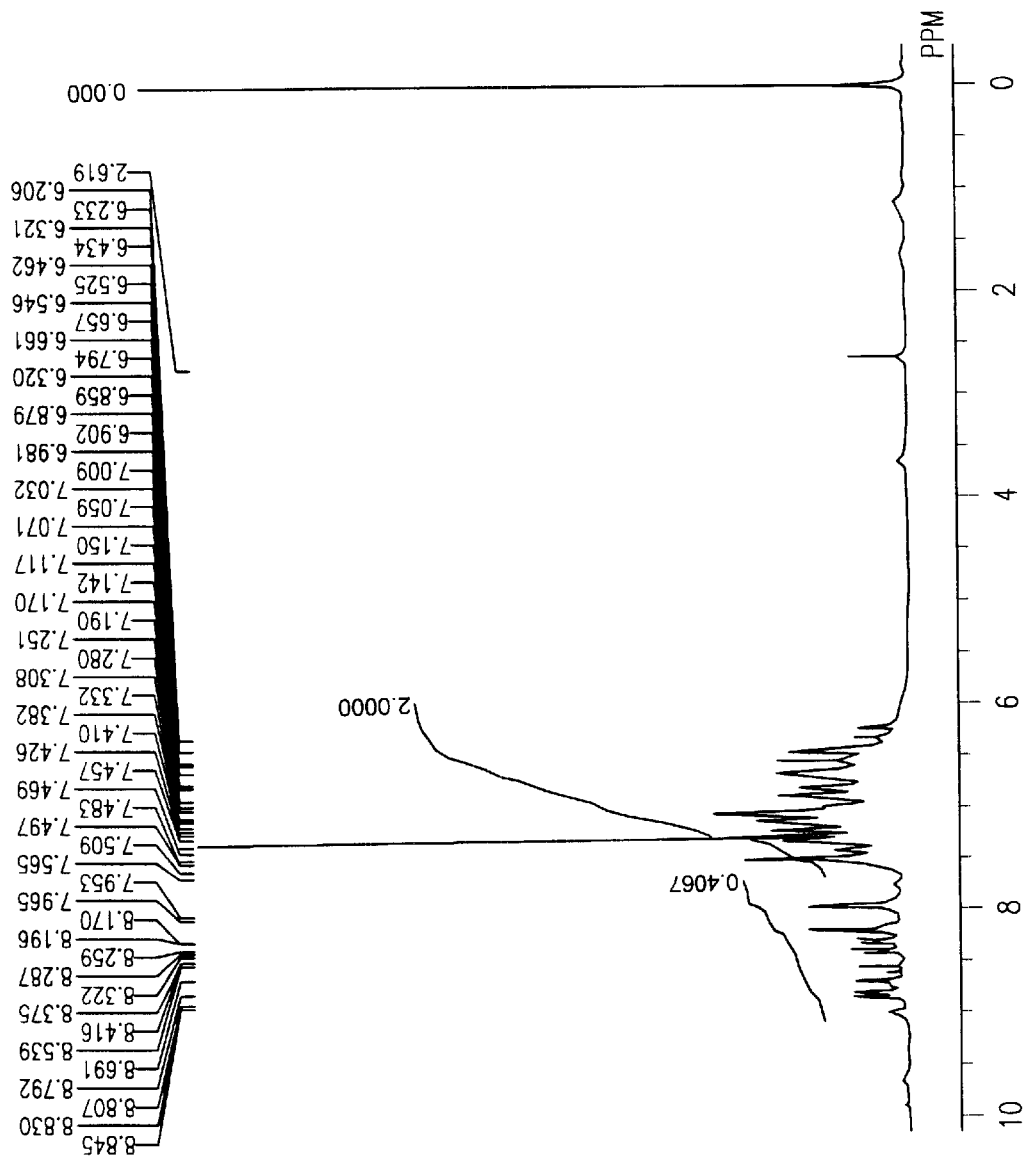
FIG. 1 is the NMR-$H^1$ spectrum of Complex 1.
Figure 2:
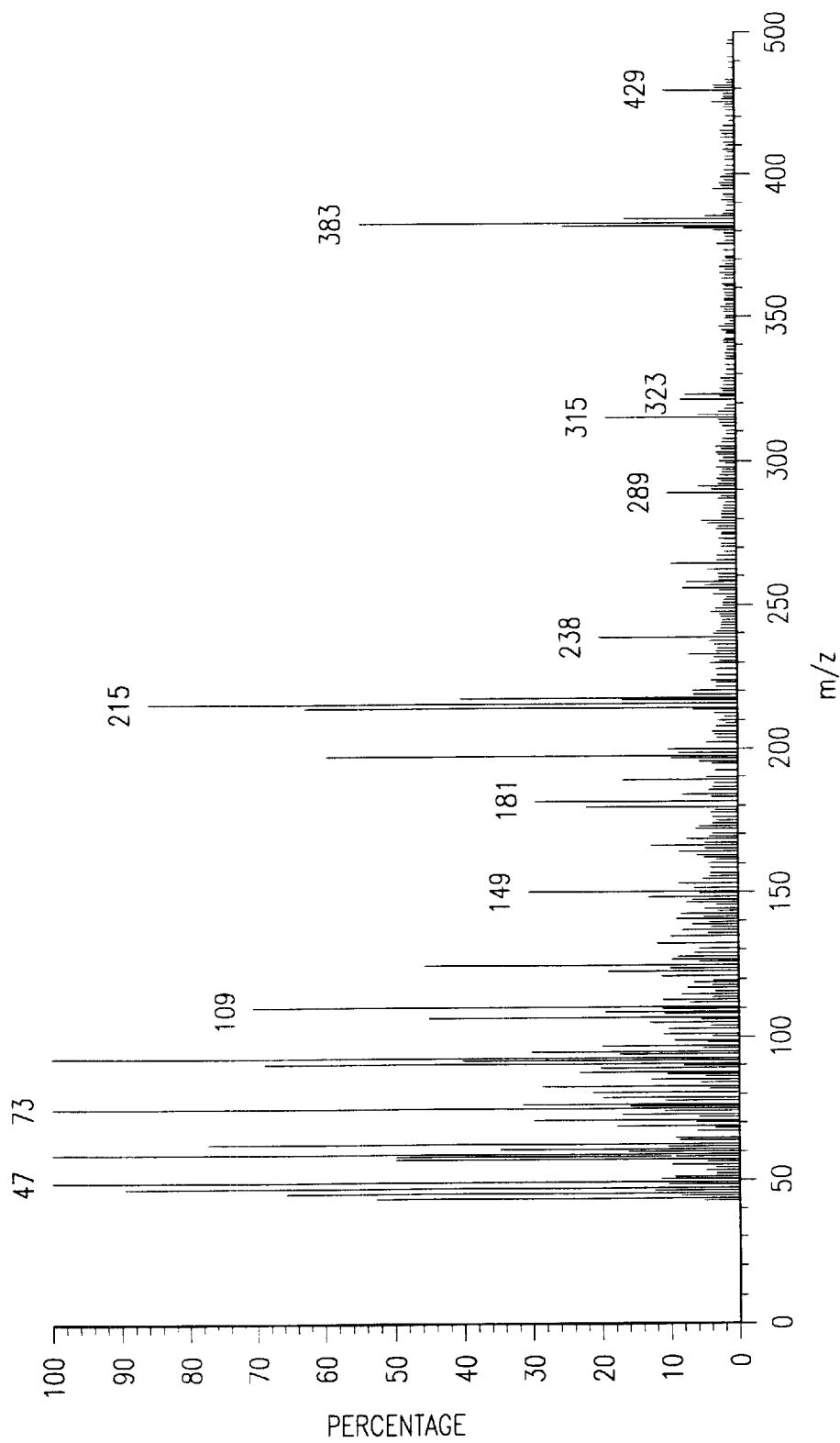
FIG. 2 is the mass spectrum of Complex 1.

In accordance with the present invention, a series of emitting materials used for organic EL based on tridentate ligands are characterized as Formula 1, Formula 2 and Formula 3. where: the group O-I-N is a bidentate ligand such as 8-hydroxyquinoline and 2-(o-hydroxyphenyl)-benzoxazole, II, III are unsubstituted or substituted aryl groups. The substituted groups can have 1–8 carbon atoms, halogen, cyano, amino, amido, sulfonyl, carbonyl, aryl, or heteroalkyl groups. The ligand including II and III is a tridentate ligand with three chelate atoms: two oxygen atoms and one nitrogen atom. The central metal atoms can be trivalent or tetravalent atoms such as Al, In, Ga, Tl, and Sn.

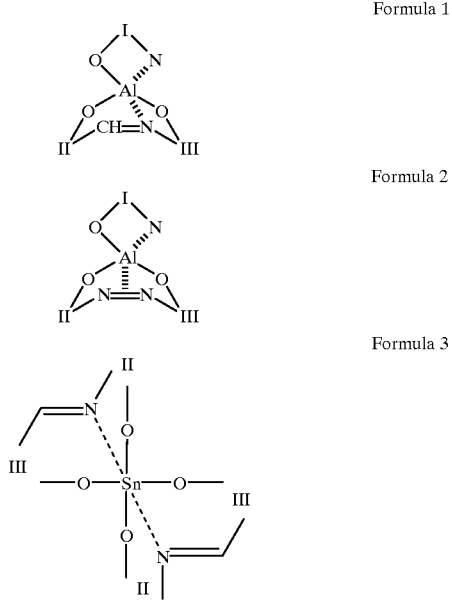

These emitting materials should possess good thermal stability and high purity. The glass transition temperature (Tg) is a key parameter to determine the stability of the amorphous materials. The high Tg could minimize the probability of the crystallization in amorphous thin films, especially under the condition of a high temperature. The Tg of tris(8-hydroxyquinoline) aluminum (Alq3) is about 175° C., far below its decomposing temperature. Almost all of these complexes according to the invention have the high Tg more than 200° C. Meanwhile, these materials can be used as emitting materials or electronic transport materials in organic EL devices.

Typical complexes of the Formula 1 were shown in below table 1.

TABLE 1

| II, III | O—I—N | | |
|---|---|---|---|
| | 8-hydroxyquinoline | 5-Cl-8-hydroxyquinoline | 2-(o-hydroxyphenyl)-benzoxazole |
| II = phenyl<br>III = phenyl | Complex 1 | Complex 2 | Complex 3 |
| II = 1,2 substituted naphthyl<br>III = phenyl | Complex 4 | Complex 5 | |
| II = 2,3 substituted naphthyl<br>III = phenyl | Complex 6 | | |
| II = 3,4 substituted naphthyl<br>III = phenyl | Complex 7 | | |
| II = phenyl<br>III = 1,2 substituted naphthyl | Complex 8 | Complex 9 | |
| II = phenyl<br>III = 2,3 substituted naphthyl | Complex 10 | | |
| II = phenyl<br>III = 3,4 substituted naphthyl | Complex 11 | | |

According to the definitions in table 1, it is obvious that the Complexes 1–11 have the following constitutional structures respectively.

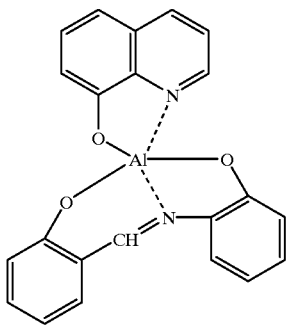

Complex 1

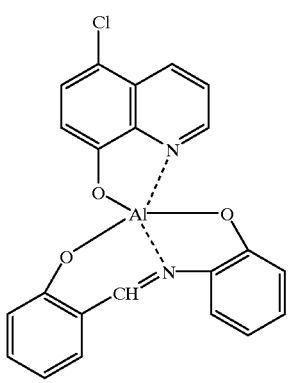

Complex 2

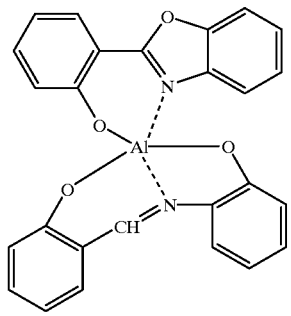

Complex 3

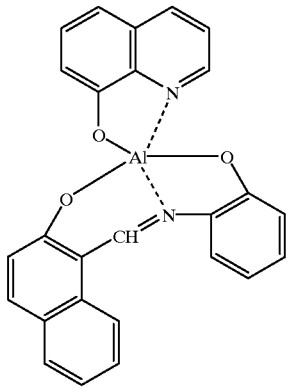

Complex 4

Complex 5
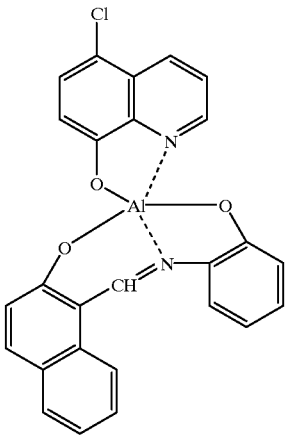
Complex 6
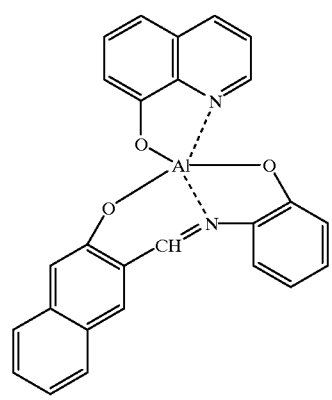
Complex 7
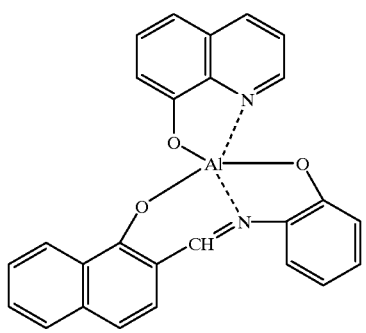
Complex 8
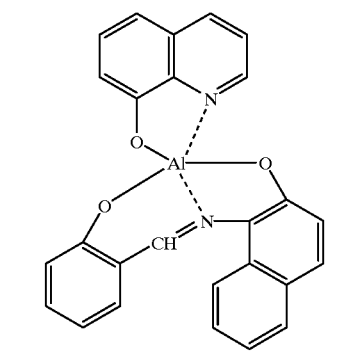
Complex 9
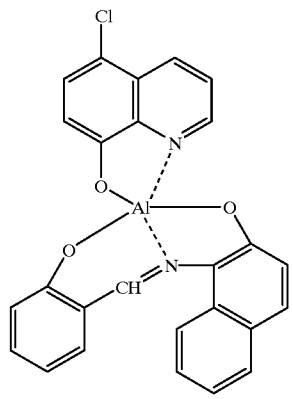
Complex 10
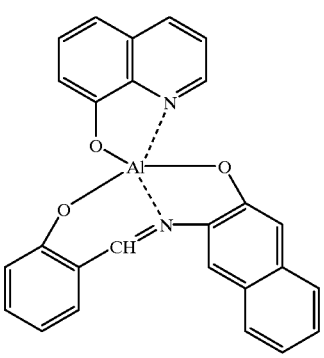
Complex 11
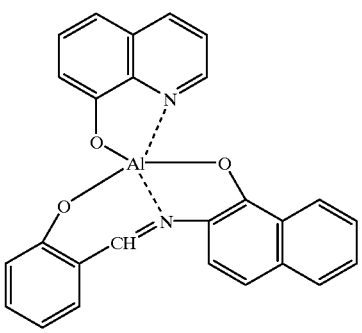
Typical complexes of the Formula 2 were shown in below table 2.

TABLE 2

| II, III | O—I—N | | |
|---|---|---|---|
| | 8-hydroxyquinoline | 5-Cl-8-hydroxyquinoline | 2-(o-hydroxyphenyl)-benzoxazole |
| L1 II = phenyl<br>III = phenyl | Complex 12 | Complex 13 | Complex 14 |
| L2 II = 1,2 substituted naphthyl<br>III = phenyl | Complex 15 | Complex 16 | |
| L3 II = 2,3 substituted naphthyl<br>III = phenyl | Complex 17 | | |
| L4 II = 3,4 substituted naphthyl<br>III = phenyl | Complex 18 | | |
| L5 II = phenyl<br>III = 1,2 substituted naphthyl | Complex 19 | Complex 20 | |
| L6 II = phenyl<br>III = 2,3 substituted naphthyl | Complex 21 | | |
| L7 II = phenyl<br>III = 3,4 substituted naphthyl | Complex 22 | | |

According to the definitions in table 2, it is obvious that the Complexes 12–22 have the following constitutional structures respectively.

Complex 12

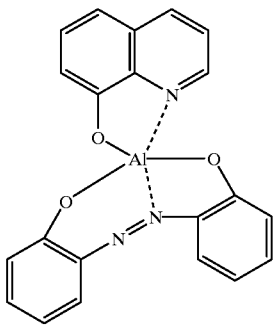

Complex 13

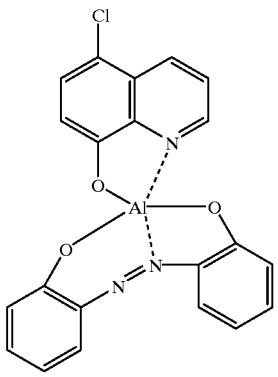

-continued

Complex 14

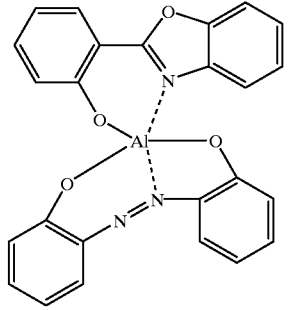

Complex 15

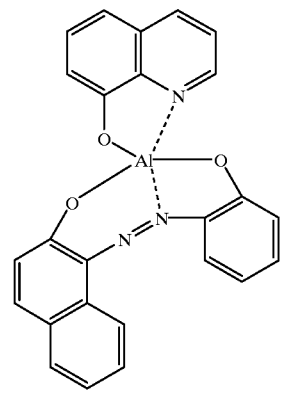

Complex 16
Complex 17
Complex 18
Complex 19
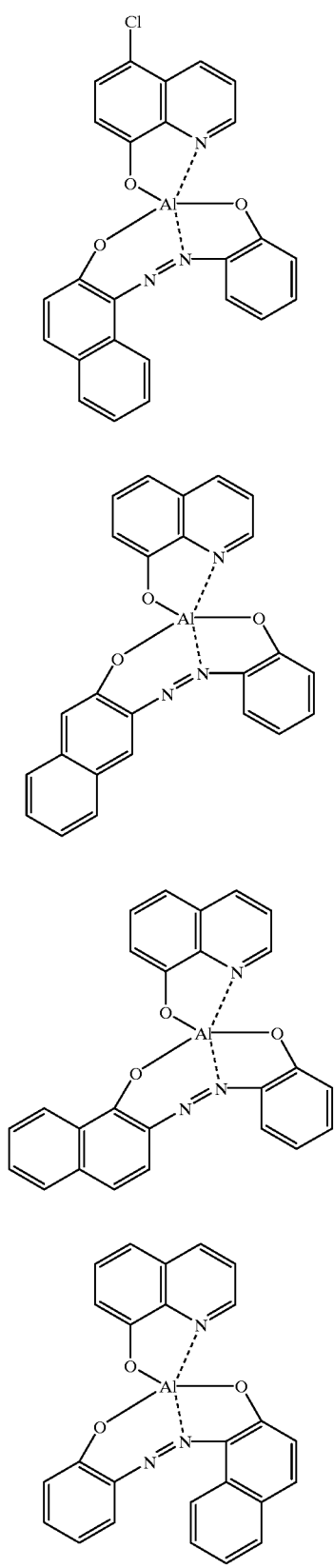
Complex 20
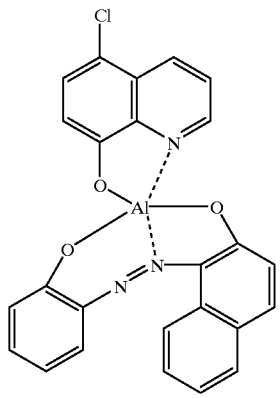
Complex 21
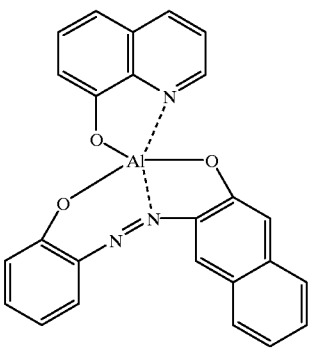
Complex 22
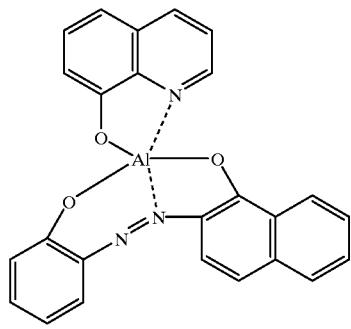
Typical complexes of the Formula 3 were shown in below table 3.

TABLE 3
| III | phenyl | 1,2-substituted naphthyl | 2,3-substituted naphthyl | 3,4 substituted naphthyl |
|---|---|---|---|---|
| phenyl | Complex 23 | Complex 27 | Complex 28 | Complex 29 |
| 1,2 substituted naphthyl | Complex 24 | | | |
| 2,3 substituted naphthyl | Complex 25 | | | |
| 3,4 substituted naphthyl | Complex 26 | | | |
According to the definitions in table 3, it is obvious that the Complexes 23–29 have the following constitutional structures respectively.
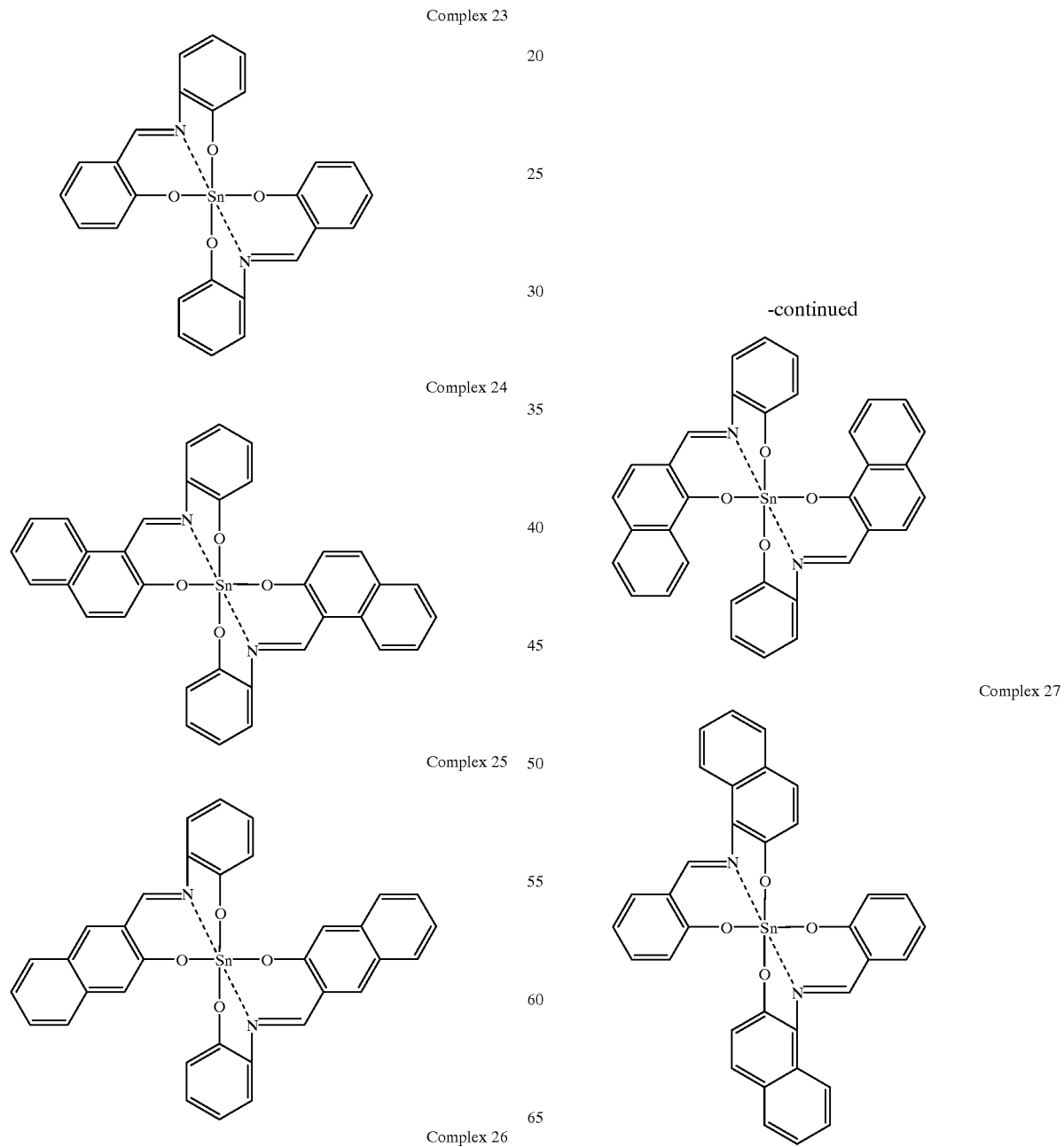

Complex 28

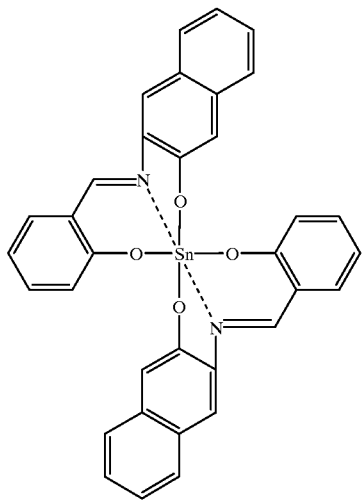

Complex 29

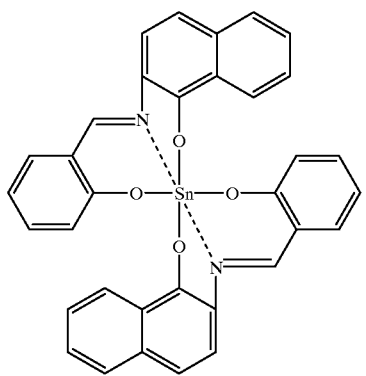

All the above these compounds can be prepared by the following two steps: the first step is the synthesis of the tridentate ligands, the second step is the synthesis of the objective complexes.

The first step is the synthesis of the tridentate ligands. The ligands described in Formula 1 and Formula 3 are shiff bases, which can be synthesized by conventional shiff base synthesis methods comprising the steps: heating the mixture of o-hydroxy-aryl aldehyde and o-hydroxy-aryl alcohol and recrystallization in an organic solvent. The ligands described in Formula 2 can be synthesized by the method of Willstatter (Anal. Chem.,35,1144).

The second step includes a chemical reaction in an organic solvent controlled by organic bases. Inorganic aluminium salts or organic aluminium compounds in solvent are added with the solution of ligands. The product was collected by filtration and washed with solvents. The compounds were further purified by the train sublimation method.

The EL devices are fabricated by conventional vacuum vapor deposition method under a vacuum condition or spin coating method at room temperature. As described above, said complexes can be used in OLEDs serving as emitting materials or electron transport materials. When used as electron transport and emitting layers in the EL devices, they are heated by conventional vacuum vapor deposition method; when used as dyes of these layers in the EL devices, they also can be treated with spin coating method.

The OLEDs are fabricated on the ITO coated glasses after carefully cleaning. The material is vaporized to form a thin layer after a thin layer of hole transport material was prepared on a glass plate. The electron transport layer is optional for OLEDs. As the last step, a thin film of metal that is used as cathode is formed by conventional vacuum vapor deposition method.

The advantage of these materials lies in their excellent thermal stability and good performance to form amorphous films. Some incompatibilities with the hole transport materials also exist in many emitting complexes that would lead to phase separation. The materials in this invention have made some progress in improving the compatibilities with other layers materials. These materials have some unique characteristics that will be conducive to forming high quality amorphous films. Such novel complexes can be used as a thermal stable emitting material for OLEDs. In addition, a series of emitting colors have been obtained from these materials including green, yellow, and red, some of which are remain rare now. And the color position in the color coordinates system shows strong potential as a red light-emitting material for organic electroluminescence. The introductions of tridentate ligands in the complex structure open a new route for exploring new materials for organic EL.

The following non-limiting example further serves to illustrate the invention.

As described below, the example 1~example 11 are directed to the preparation and use of Complex 1~Complex 11.

EXAMPLE 1

Complex 1

Figure 3:
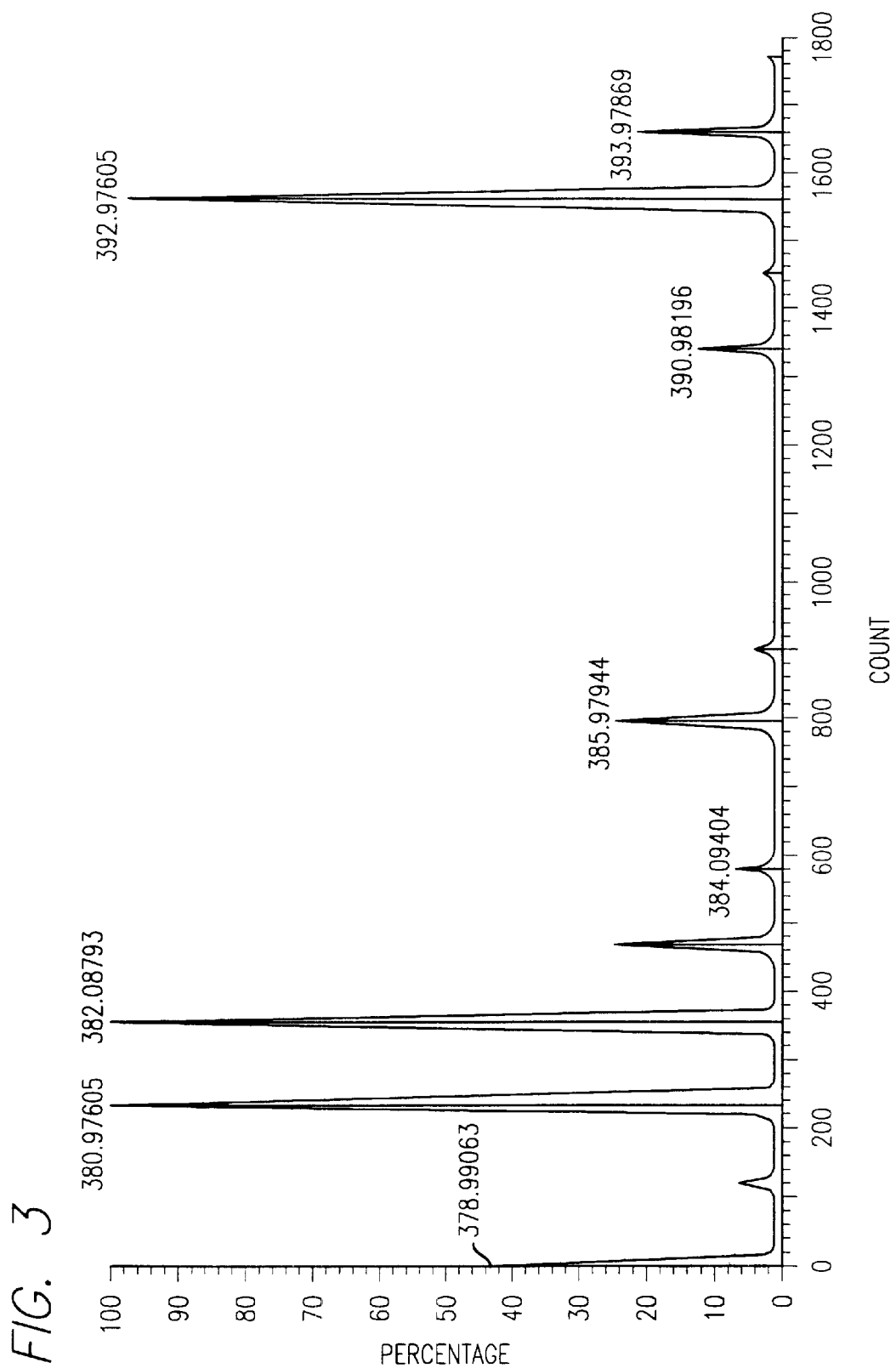
FIG. 3 is the high-resolution mass spectrum of Complex 1.

Synthesis of the Complex 1:

Complex 1 was synthesized through a reaction in the ethanol solution of 8-hydroxyquinoline, salicylidene-o-aminophenol and $AlCl_3$ as follows. First, a solution of 8-hydroxyquinoline (0.05M) and piperidine (0.05M) in 100 ml ethanol was added to a solution of $AlCl_3.6H_2O$ (0.5M) in 10 ml ethanol very slowly with an intensive stirring. Then, a solution of salicylidene-o-aminophenol (0.01M) and piperidine (0.02M) in 500 ml ethanol was introduced slowly. The mixture was stirred for about 1 hour and cooled to room temperature and kept in dark for about 10 hours. A yellow precipitate was formed when equivalent amount water was poured into the solution. The product was collected by filtration and washed with ethanol rapidly, then dried under an infrared lamp. The obtained product power showed strong yellow fluorescence under an ultraviolet lamp. The materials were further purified by an improved train sublimation method. The salicylidene-o-aminophenol ligand was obtained by heating the mixture of 2-aminophenol and 2-hydroxy-salicylic aldehyde in ethanol solution and the following recrystallization. The molecular structure of Complex 1 was supported by high-resolution mass spectrum (MS) shown in FIG. 3, nuclear magnetic resonance (NMR) shown in FIG. 1 and element analysis. High-resolution MS found: 382.08793. Calc. for C22H15O3N2Al: 382.08981 (shown in FIG. 4); Element analysis found: C, 68.85; H, 3.83; N, 7.17, Calc. For Complex 1: C, 69.11, H, 39.3; N, 7.33.

Fabrication of four EL devices with complex 1:

1. (device 1) The EL device was fabricated by conventional vacuum vapor deposition method under a $2\times10^{-3}$ Pa vacuum at room temperature. For example, the methods can be found in the following references: C. W. Tang and S. A. Vanslyke: Appl. Phys. Lett. 51 (1987) 913; Zilan Shen, Paul E. Burrows, Vladimir Bulovic, Stephen R. Forrest and Mark E. Thompson: Science 276(1997) 2009; Philip S. Bryan, Frank V. Lovecchio, Steven A. Vanslyke, Rochester: U.S. Pat. No. 5,141,671 (1992). N,N'-diphenyl-N,N'-di(m-methylphenyl) benzidine (TPD) was used as the hole transport layer material. The following layer structures of were prepared: indium-tin-oxide (ITO)/TPD (60 nm)/Complex 1 (40 nm)/MgAg (10:1). The maximum brightness of the device was up to 2000 cd/m$^2$. The EL emission was at around 573 nm and the maximum luminous efficiencies up to 1.5 lm/W, which was shown in table 5.

2. (device 2) The EL device was fabricated by conventional vacuum vapor deposition method under a 2×10−3 Pa vacuum at room temperature. N,N'-diphenyl-N,N'-di(m-methylphenyl) benzidine (TPD) was used as the hole transport layer material. The following layer structure of devices was prepared: ITO/TPD (60 nm)/Complex 1 (40 nm)/Alq3 (20 nm)/MgAg (10:1). The maximum brightness of the device was up to 3000 cd/m$^2$. The EL emission was at around 573 nm and the maximum luminous efficiencies up to 1.7 lm/W, which was shown in table 5.

3. (device 3) The EL device was fabricated by conventional vacuum vapor deposition method under a 2×10−3 Pa vacuum at room temperature. N,N'-diphenyl-N,N'-di(m-methylphenyl) benzidine (TPD) was used as the hole transport layer material. The following layer structures of was prepared: ITO/TPD; Complex 1 (100:1~15:1 by weight) (60 nm)/Alq3 (40 nm)/MgAg (10:1). The maximum brightness of the device was up to 2500 cd/m$^2$. The EL emission was at 535~577 nm (depending on the concentration of Complex 1 in the thin film) and the maximum luminous efficiencies up to 1.8 lm/W, which was shown in table 5.

4. (device 4) Both Complex 1 and some polymer (such as poly(N-vinylcarbazole) (PVK)) were dissolved in some organic solvent (such as C2H4Cl2). The thin film of mixture of Complex 1 and polymer was prepared by spin coating method. The following layer structures of was prepared: ITO/PVK: Complex 1 (100:1~15:1 by weight) (60 nm)/Alq3 (40 nm)/MgAg (10:1). The maximum brightness of the device was up to 1800 cd/m$^2$. The EL emission was at 505~573 nm (depending on the concentration of Complex 1 in the thin film) and the maximum luminous efficiencies up to 1.8 lm/W, which was shown in table 5.

EXAMPLE 2

Complex 2

According to the synthesis procedures of Complex 1, Complex 2 was prepared by replacing 8-hydroxyquinoline with 5-Cl-8-hydroxyquinoline. The data for identifying this complex was shown in the following table 4.

The four kinds of devices were prepared similar to the processes of Complex 1. The performances of these devices were shown in the following table 5.

EXAMPLE 3

Complex 3

According to the synthesis procedures of Complex 1, Complex 3 was prepared by replacing 8-hydroxyquinoline with 2-(o-hydroxyphenyl)-benzoxazole. The data for identifying this complex was shown in the following table 4.

The four kinds of devices were prepared similar to the processes of Complex 1. The performances of these devices were shown in the following table 5.

EXAMPLE 4

Complex 4

According to the synthesis procedures of Complex 1, Complex 4 was prepared by replacing 2-hydroxy-salicylic aldehyde with 2-hydroxy-naphthyl aldehyde. The data for identifying this complex was shown in the following table 4.

EXAMPLE 5

Complex 5

According to the synthesis procedures of Complex 4, Complex 5 was prepared by replacing 8-hydroxyquinoline with 5-Cl-8-hydroxyquinoline. The data for identifying this complex was shown in the following table 4.

EXAMPLE 6

Complex 6

According to the synthesis procedures of Complex 4, Complex 6 was prepared by replacing 2-hydroxy-naphthyl aldehyde with 3-hydroxy-2-naphthyl aldehyde. The data for identifying this complex was shown in the following table 4.

EXAMPLE 7

Complex 7

According to the synthesis procedures of Complex 4, Complex 7 was prepared by replacing 2-hydroxy-naphthyl aldehyde with 1-hydroxy-2-naphthyl aldehyde. The data for identifying this complex was shown in the following table 4.

EXAMPLE 8

Complex 8

According to the synthesis procedures of Complex 4, Complex 8 was prepared by replacing 2-aminophenol with 2-hydroxy-1-naphthyl amine. The data for identifying this complex was shown in the following table 4.

EXAMPLE 9

Complex 9

According to the synthesis procedures of Complex 8, Complex 9 was prepared by replacing 8-hydroxyquinoline with 5-Cl-8-hydroxyquinoline. The data for identifying this complex was shown in the following table 4.

EXAMPLE 10

Complex 10

According to the synthesis procedures of Complex 4, Complex 10 was prepared by replacing 2-aminophenol with 3-hydroxy-2-naphthyl amine. The data for identifying this complex was shown in the following table 4.

EXAMPLE 11

Complex 11

According to the synthesis procedures of Complex 4, Complex 11 was prepared by replacing 2-aminophenol with 1-hydroxy-2-naphthyl amine. The data for identifying this complex was shown in the following table 4.

TABLE 4

| Complex No. | Production yield % | Cal. for Structural Formula | | | Element analysis | | |
|---|---|---|---|---|---|---|---|
| | | C % | H % | N % | C % | H % | N % |
| 1 | 75 | 69.11 | 3.93 | 7.33 | 68.8 | 3.8 | 7.17 |
| 2 | 68 | 63.39 | 3.36 | 6.72 | 62.9 | 3.27 | 6.82 |
| 3 | 70 | 69.64 | 3.80 | 6.25 | 70.2 | 3.79 | 6.20 |
| 4 | 74 | 72.22 | 3.94 | 6.48 | 73.1 | 3.82 | 6.56 |
| 5 | 64 | 66.88 | 3.43 | 6.00 | 67.7 | 3.29 | 6.18 |
| 6 | 72 | 72.22 | 3.94 | 6.48 | 72.7 | 3.84 | 6.53 |
| 7 | 63 | 72.22 | 3.94 | 6.48 | 73.1 | 3.86 | 6.51 |
| 8 | 74 | 72.22 | 3.94 | 6.48 | 73.4 | 3.83 | 6.54 |
| 9 | 69 | 66.88 | 3.43 | 6.00 | 67.1 | 3.40 | 6.11 |
| 10 | 66 | 72.22 | 3.94 | 6.48 | 72.9 | 3.89 | 6.53 |
| 11 | 61 | 72.22 | 3.94 | 6.48 | 73.2 | 3.88 | 6.50 |

TABLE 5

| Device No. | | Complex 1 | Complex 2 | Complex 3 |
|---|---|---|---|---|
| 1 | Brightness /cd/m$^2$ (12V) | 2000 | 800 | 600 |
| | The maximum wavelength/nm | 573 | 568 | 563 |
| 2 | Brightness /cd/m$^2$ (12V) | 3000 | 1000 | 900 |
| | The maximum wavelength/nm | 573 | 567 | 562 |
| 3 | Brightness /cd/m$^2$ (12V) | 2500 | >1500 | >1100 |
| | The maximum wavelength/nm | 535~577 | 537~569 | 538~566 |
| 4 | Brightness /cd/m$^2$ (12V) | 1800 | >1200 | >860 |
| | The maximum wavelenghth/nm | 505~573 | 531~569 | 537~564 |

The following example 12~example 22 are directed to the preparation and use of Complex 12~Complex 22, in which L1~L7 represent the tridentate ligands listed in table 2.

EXAMPLE 12

Complex 12

Figure 5:
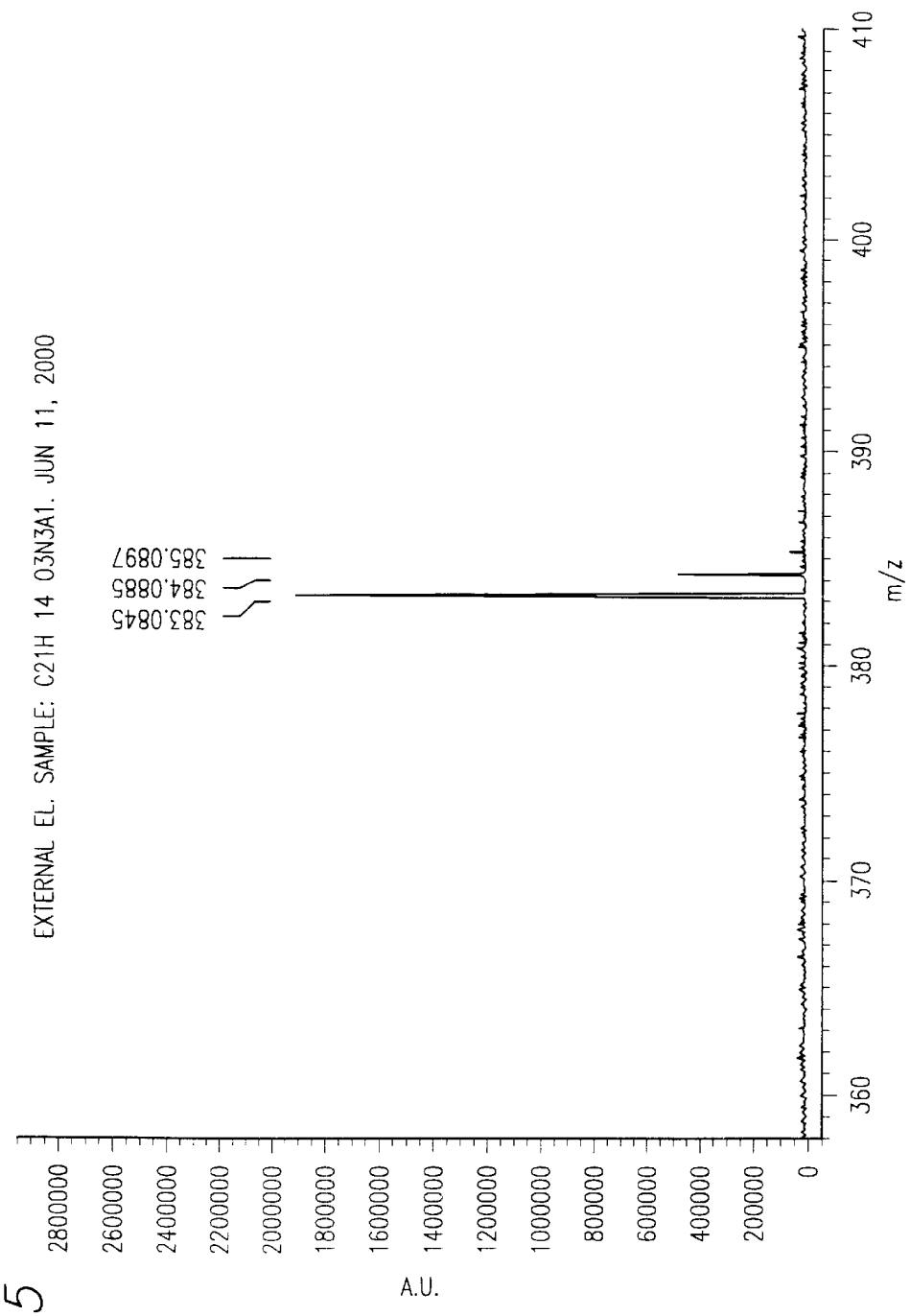
FIG. 5 is the high-resolution mass spectrum of Complex 12.
Figure 7:
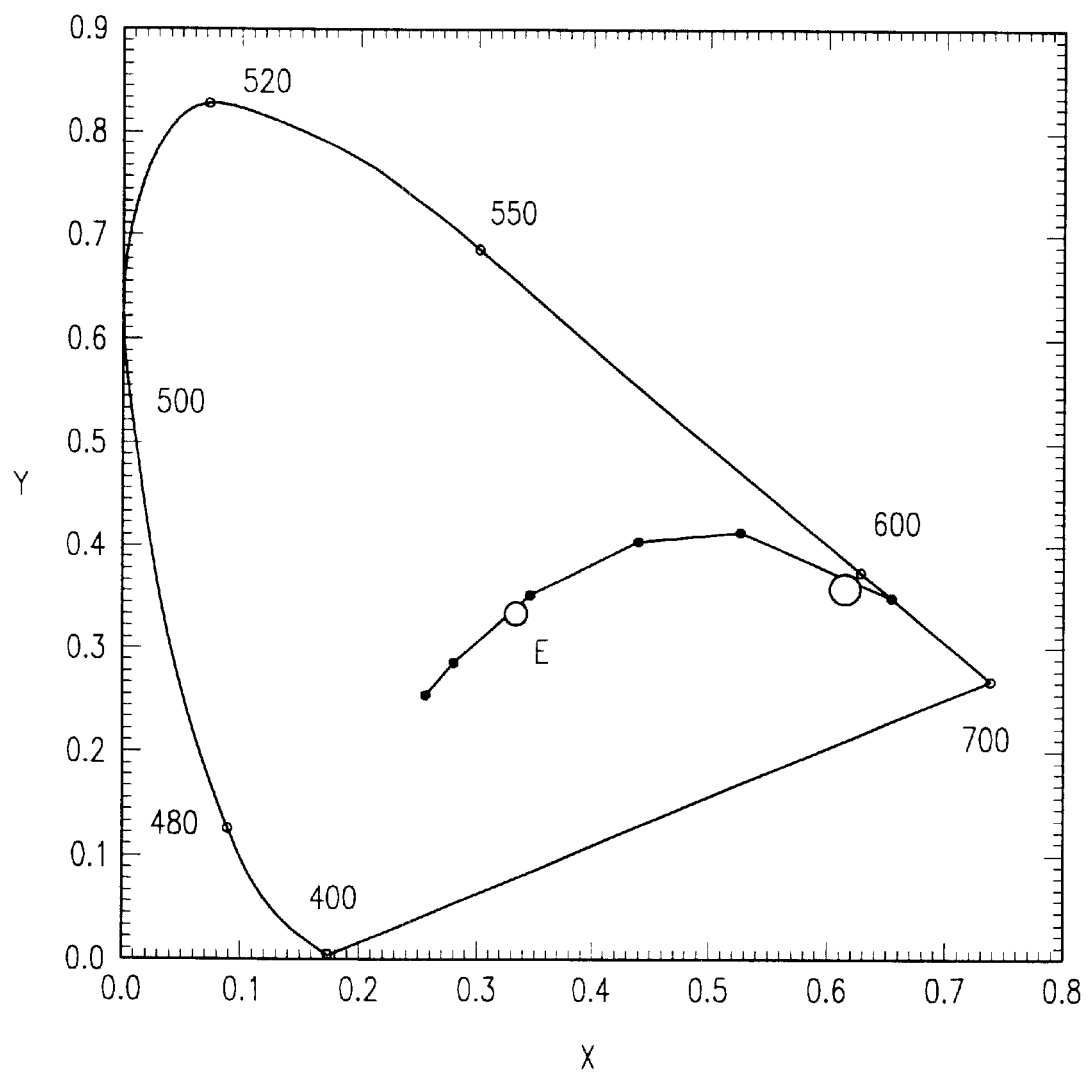
FIG. 7 is the color position in the color coordinates system (CIE 1931) for the device 3 comprising Complex 12, with the following layer structure: ITO/TPD/Complex 12 (100:1~15:1 by weight) (60 nm)/Alq3 (40 nm)/MgAg (10:1).

Synthesis of the Complex 12:

Complex 12 was synthesized through a reaction in the ethanol solution of 8-hydroxyquinoline, o,o'-dihydroxyazobenzene (L1) and AlCl$_3$. First, a solution of 8-hydroxyquinoline (0.05M) and piperidine (0.05M) in 100 ml ethanol was added to a solution of AlCl$_3$.6H$_2$O (0.5M) in 10 ml ethanol very slowly with an intensive stirring. Then, a solution of L1 (0.01M) and piperidine (0.02M) in 500 ml ethanol was introduced slowly. The mixture was stirred for about 1 hour and cooled to room temperature and kept in dark for about 10 hours. A scarlet precipitate was formed when equivalent amount water was poured into the solution. The product was collected by filtration and washed with ethanol rapidly, then dried under an infrared lamp. The obtained product power showed strong red fluorescence under an ultraviolet lamp. The materials were further purified by an improved train sublimation method. The L1 ligand was obtained by typical synthesis method of azobenzene. The molecular structure of Complex 12 was supported by high-resolution mass spectrum (MS) shown in FIG. 5 and element analysis. High-resolution MS found: 383.0845240. Calc. for C21H14O3N3Al: 383.0845062 (shown in FIG. 6); Element analysis found: C, 65.9; H, 3.89; N, 10.68, Calc. For Complex 12: C, 65.80, H, 3.66; N, 10.97.

Fabrication of four EL devices with complex 12:

1. (device 1) The EL device was fabricated by conventional vacuum vapor deposition method under a 2×10−3 Pa vacuum at room temperature. N,N'-diphenyl-N,N'-di(m-methylphenyl) benzidine (TPD) was used as the hole transport layer material. The following layer structures of was prepared: ITO/TPD (60 nm)/Complex 12 (40 nm)/MgAg (10:1). The maximum brightness of the device was up to 120 cd/m$^2$ and the EL emission was at around 640 nm, which was shown in table 8.

2. (device 2) The EL device was fabricated by conventional vacuum vapor deposition method under a 2×10−3 Pa vacuum at room temperature. N,N'-diphenyl-N,N'-di(m-methylphenyl) benzidine (TPD) was used as the hole transport layer material. The following layer structures of was prepared: ITO/TPD (60 nm)/Complex 12 (40 nm)/Alq3 (20 nm)/MgAg (10:1). The maximum brightness of the device was up to 150 cd/m$^2$ and the EL emission was at around 635 nm, which was shown in table 8.

3. (device 3) The EL device was fabricated by conventional vacuum vapor deposition method under a 2×10−3 Pa vacuum at room temperature. N,N'-diphenyl-N,N'-di(m-methylphenyl) benzidine (TPD) was used as the hole transport layer material. The following layer structures of was prepared: ITO/TPD: Complex 12 (100:1~15:1 by weight) (60 nm)/Alq3 (40 nm)/MgAg (10:1). The maximum brightness of the device was up to 150 cd/m$^2$ and the EL emission was at 625~645 nm (depending on the concentration of Complex 1 in the thin film), which was shown in table 8.

4. (device 4) Both Complex 1 and some polymer (such as PVK) were dissolved in some organic solvent (such as C2H4Cl2). The thin film of mixture of Complex 1 and polymer was prepared by spin coating method. The following layer structures of was prepared: ITO/PVK: Complex 12 (100:1~15:1 by weight) (60 nm)/Alq3 (40 nm)/MgAg (10:1). The maximum brightness of the device was up to 130 cd/m$^2$ and the EL emission was at 605~645 nm (depending on the concentration of Complex 1 in the thin film), which was shown in table 8.

EXAMPLE 13

Complex 13

According to the synthesis procedures of Complex 12, Complex 13 was prepared by replacing 8-hydroxyquinoline with 5-Cl-8-hydroxyquinoline. The data for identifying this complex was shown in the following table 7.

EXAMPLE 14

Complex 14

According to the synthesis procedures of Complex 12, Complex 14 was prepared by replacing 8-hydroxyquinoline with 2-(o-hydroxyphenyl)-benzoxazole. The data for identifying this complex was shown in the following table 7.

EXAMPLE 15

Complex 15

According to the synthesis procedures of Complex 12, Complex 15 was prepared by replacing L1 with L2. The data for identifying this complex was shown in the following table 7.

EXAMPLE 16

Complex 16

According to the synthesis procedures of Complex 15, Complex 16 was prepared by replacing 8-hydroxyquinoline with 5-Cl-8-hydroxyquinoline. The data for identifying this complex was shown in the following table 7.

EXAMPLE 17

Complex 17

According to the synthesis procedures of Complex 15, Complex 17 was prepared by replacing L1 with L3. The data for identifying this complex was shown in the following table 7.

EXAMPLE 18

Complex 18

According to the synthesis procedures of Complex 15, Complex 18 was prepared by replacing L1 with L4. The data for identifying this complex was shown in the following table 7.

EXAMPLE 19

Complex 19

According to the synthesis procedures of Complex 15, Complex 19 was prepared by replacing L1 with L5. The data for identifying this complex was shown in the following table 7.

EXAMPLE 20

Complex 20

According to the synthesis procedures of Complex 19, Complex 20 was prepared by replacing 8-hydroxyquinoline with 5-Cl-8-hydroxyquinoline. The data for identifying this complex was shown in the following table 7.

EXAMPLE 21

Complex 21

According to the synthesis procedures of Complex 15, Complex 21 was prepared by replacing L1 with L6. The data for identifying this complex was shown in the following table 7.

EXAMPLE 22

Complex 22

According to the synthesis procedures of Complex 15, Complex 22 was prepared by replacing L1 with L7. The data for identifying this complex was shown in the following table 7.

TABLE 7

| Complex No. | Production yield % | Cal. for Structural Formula | | | Element analysis | | |
|---|---|---|---|---|---|---|---|
| | | C % | H % | N % | C % | H % | N % |
| 12 | 78 | 65.80 | 3.66 | 10.97 | 65.9 | 3.89 | 10.68 |
| 13 | 66 | 60.36 | 3.11 | 10.06 | 60.4 | 3.32 | 10.22 |
| 14 | 65 | 66.82 | 9.35 | 6.25 | 66.6 | 3.80 | 9.31 |
| 15 | 69 | 69.28 | 3.70 | 9.70 | 68.9 | 3.88 | 9.86 |
| 16 | 67 | 64.17 | 3.21 | 8.98 | 64.0 | 3.33 | 8.91 |
| 17 | 75 | 69.28 | 3.70 | 9.70 | 68.9 | 3.87 | 9.82 |
| 18 | 70 | 69.28 | 3.70 | 9.70 | 69.3 | 3.79 | 9.65 |
| 19 | 77 | 69.28 | 3.70 | 9.70 | 69.1 | 3.84 | 9.68 |
| 20 | 74 | 64.17 | 3.21 | 8.98 | 64.2 | 3.36 | 8.89 |
| 21 | 73 | 69.28 | 3.70 | 9.70 | 68.9 | 3.79 | 9.62 |
| 22 | 75 | 69.28 | 3.70 | 9.70 | 68.8 | 3.80 | 9.67 |

TABLE 8

| Device No. | | Complex 12 |
|---|---|---|
| 1 | Brightness /cd/m$^2$ (25V) | 120 |
| | The maximum wavelength/nm | 640 |
| 2 | Brightness /cd/m$^2$ (25V) | 150 |
| | The maximum wavelength/nm | 635 |
| 3 | Brightness /cd/m$^2$ (25V) | 150 |
| | The maximum wavelength/nm | 625~645 |
| 4 | Brightness /cd/m$^2$ (25V) | 130 |
| | The maximum wavelength/nm | 605~645 |

The following example 23~example 29 are directed to Complex 23~Complex 29. All the tridentate ligands are the same as the tridentate ligands used in the first group complexes. So the synthesis of these ligands are referred to the example 1~example 11.

EXAMPLE 23

Complex 23

Synthesis of the Complex 23:

Complex 23 was synthesized through a reaction in the ethanol solution of salicylidene-o-aminophenol and SnCl$_4$. The salicylidene-o-aminophenol ligand was obtained by heating the mixture of 2-aminophenol and 2-hydroxy-salicylic aldehyde in ethanol solution and the following recrystallization. A solution of salicylidene-o-aminophenol (0.01M) and piperidine (0.02M) in 500 ml ethanol was added to a solution of SnCl$_4$ (0.25M) in 10 ml ethanol very slowly with an intensive stirring. A light yellow precipitate was formed. The mixture was stirred for about 1 hour and cooled to room temperature and kept in dark for about 10 hours. The product was collected by filtration and washed with ethanol rapidly, then dried under an infrared lamp. The obtained product power showed strong yellow fluorescence under an ultraviolet lamp. The materials were further purified by an improved train sublimation method. The molecular structure of Complex 23 was supported by element analysis. Element analysis found: C, 57.68; H, 3.34; N, 5.18, Calc. For Complex 23: C, 57.703, H, 3.329; N, 5.178.

Figure 8:
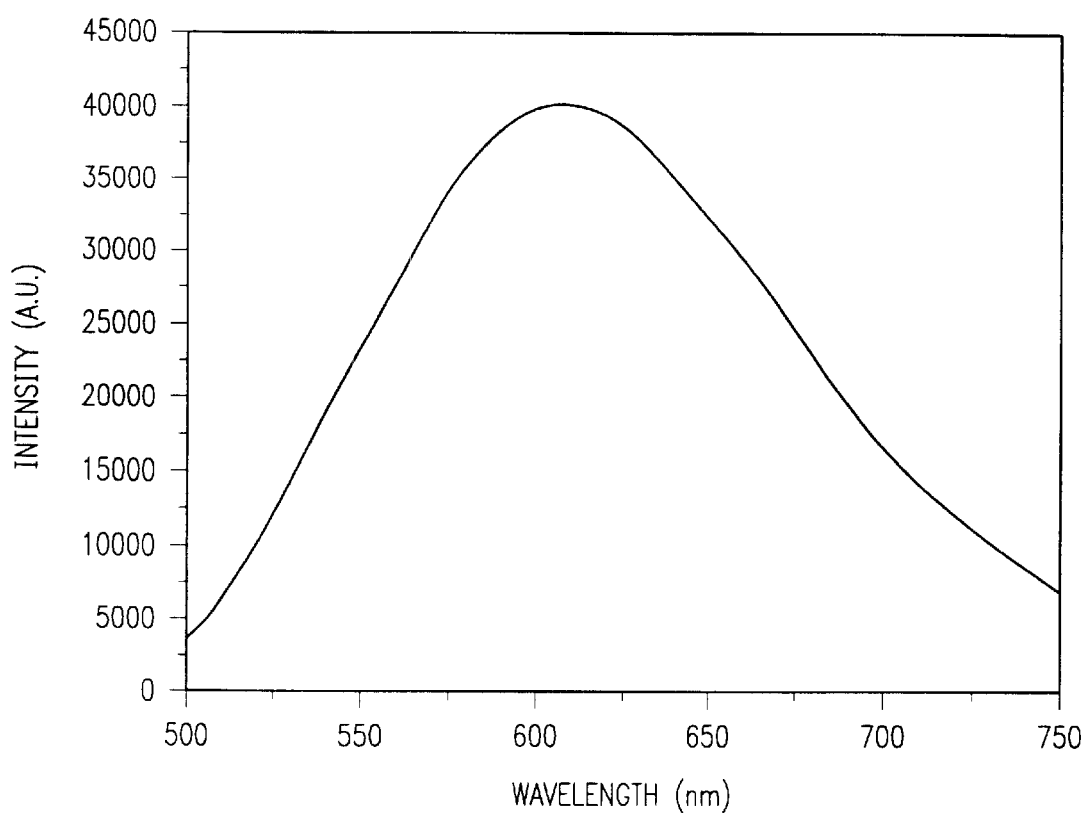
FIG. 8 is the EL spectra for the device 1 comprising Complex 23, with the following layer structure: ITO/TPD (60 nm)/Complex 23/MgAg (10:1)

Fabrication of devices with complex 23:

1. (device 1) The EL device was fabricated by conventional vacuum vapor deposition method under a 2×10−3 Pa vacuum at room temperature. N,N'-diphenyl-N,N'-di(m-methylphenyl) benzidine (TPD) was used as the hole transport layer material. The following layer structures of was prepared: ITO/TPD (60 nm)/Complex 23 (40 nm)/MgAg (10:1). The maximum brightness of the device was up to 2000 cd/m². The EL emission was at around 573 nm and the maximum luminous efficiencies up to 1.5 lm/W, which was shown in FIG. 8 and in table 10.

2. (device 2) The EL device was fabricated by conventional vacuum vapor deposition method under a 2×10−3 Pa vacuum at room temperature. N,N'-diphenyl-N,N'-di(m-methylphenyl) benzidine (TPD) was used as the hole transport layer material. The following layer structures of was prepared: ITO/TPD (60 nm)/Complex 23 (40 nm)/Alq3 (20 nm)/MgAg (10:1). The maximum brightness of the device was up to 3000 cd/m². The EL emission was at around 573 nm and the maximum luminous efficiencies up to 1.7 lm/W, which was shown in table 10.

3. (device 3) The EL device was fabricated by conventional vacuum vapor deposition method under a 2×10−3 Pa vacuum at room temperature. N,N'-diphenyl-N,N'-di(m-methylphenyl) benzidine (TPD) was used as the hole transport layer material. The following layer structures of was prepared: ITO/TPD: Complex 23 (100:1~15:1 by weight) (60 nm)/Alq3 (40 nm)/MgAg (10:1). The maximum brightness of the device was up to 2500 cd/m². The EL emission was at 535~577 nm (depending on the concentration of Complex 1 in the thin film) and the maximum luminous efficiencies up to 1.8 lm/W, which was shown in table 10.

4. (device 4) Both Complex 23 and some polymer (such as PVK) were dissolved in some organic solvent (such as C2H4Cl2). The thin film of mixture of Complex 1 and polymer was prepared by spin coating method. The following layer structures of was prepared: ITO/PVK: Complex 1 (100:1~15:1 by weight) (60 nm)/Alq3 (40 nm)/MgAg (10:1). The maximum brightness of the device was up to 1800 cd/m². The EL emission was at 505~573 nm (depending on the concentration of Complex 1 in the thin film) and the maximum luminous efficiencies up to 1.8 lm/W, which was shown in table 10.

EXAMPLE 24

Complex 24

According to the synthesis procedures of Complex 23, Complex 24 was prepared by replacing 2-hydroxy-salicylic aldehyde with 2-hydroxy-naphthyl aldehyde. The data for identifying this complex was shown in the following table 9.

EXAMPLE 25

Complex 25

According to the synthesis procedures of Complex 23, Complex 25 was prepared by replacing 2-hydroxy-naphthyl aldehyde with 3-hydroxy-2-naphthyl aldehyde. The data for identifying this complex was shown in the following table 9.

EXAMPLE 26

Complex 26

According to the synthesis procedures of Complex 23, Complex 26 was prepared by replacing 2-hydroxy-naphthyl aldehyde with 1-hydroxy-2-naphthyl aldehyde. The data for identifying this complex was shown in the following table 9.

EXAMPLE 27

Complex 27

According to the synthesis procedures of Complex 23, Complex 27 was prepared by replacing 2-aminophenol with 2-hydroxy-1-naphthyl amine. The data for identifying this complex was shown in the following table 9.

EXAMPLE 28

Complex 28

According to the synthesis procedures of Complex 23, Complex 28 was prepared by replacing 2-aminophenol with 3-hydroxy-2-naphthyl amine. The data for identifying this complex was shown in the following table 9.

EXAMPLE 29

Complex 29

According to the synthesis procedures of Complex 23, Complex 29 was prepared by replacing 2-aminophenol and 1-hydroxy-2-naphthyl amine. The data for identifying this complex was shown in the following table 9.

| Complex No. | Production yield % | Cal. for Structural Formula | | | Element analysis | | |
|---|---|---|---|---|---|---|---|
| | | C % | H % | N % | C % | H % | N % |
| 23 | 89 | 57.70 | 3.33 | 5.18 | 57.68 | 3.34 | 5.18 |
| 24 | 82 | 60.94 | 3.386 | 4.740 | 60.76 | 3.42 | 4.80 |
| 25 | 79 | 60.94 | 3.386 | 4.740 | 60.81 | 3.43 | 4.79 |
| 26 | 80 | 60.94 | 3.386 | 4.740 | 60.77 | 3.46 | 4.81 |
| 27 | 63 | 60.94 | 3.386 | 4.740 | 60.72 | 3.38 | 4.78 |
| 28 | 71 | 60.94 | 3.386 | 4.740 | 60.69 | 3.49 | 4.88 |
| 29 | 61 | 60.94 | 3.386 | 4.740 | 60.73 | 3.50 | 4.82 |

TABLE 10

| Device No. | | Complex 23 |
|---|---|---|
| 1 | Brightness /cd/m² (25V) | 85 |
| | The maximum wavelength/nm | 606 |
| 2 | Brightness /cd/m² (25V) | 160 |
| | The maximum wavelength/nm | 605 |
| 3 | Brightness /cd/m² (25V) | 210 |
| | The maximum wavelength/nm | 575~615 |
| 4 | Brightness /cd/m² (25V) | 160 |
| | The maximum wavelength/nm | 565~615 |

What is claimed is:

1. A compound of Formula 1 wherein the group O-I-N is a bidentate ligand, and II and III are unsubstituted or substituted aryl groups.

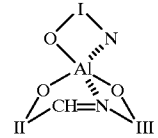

Formula 1

2. A compound of Formula 2 wherein the group O-I-N is a bidentate ligand, and II and III are unsubstituted or substituted aryl groups.

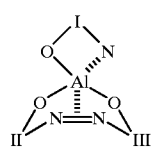

Formula 2

3. A compound of Formula 3 wherein II and III are unsubstituted or substituted aryl groups.

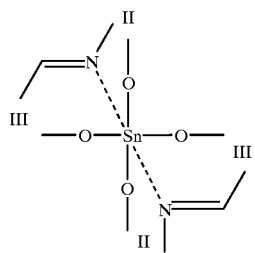

Formula 3

4. The compound of claim 1 wherein the substituents of the bidentate ligand or the aryl group II or III are independently selected from the group consisting of 1–8 carbon atoms, halogen, cyano, amino, amido, sulfonyl, carbonyl, aryl, and heteroalkyl groups.

5. The compound of claim 2 wherein the substituents of the bidentate ligand or the aryl group II or III are independently selected from the group consisting of 1–8 carbon atoms, halogen, cyano, amino, amido, sulfonyl, carbonyl, aryl, and heteroalkyl groups.

6. The compound of claim 3 wherein the subsituents of the aryl groups II or III are independently selected from the group consisting of 1–8 carbon atoms, halogen, cyano, amino, amido, sulfonyl, carbonyl, aryl, or heteroalkyl groups.

7. A yellow fluorescent material comprising a compound according to claim 1.

8. A red fluorescent material comprising a compound according to claim 2.

9. A yellow fluorescent material comprising a compound according to claim 3.

10. The compound of claim 1, wherein the bidentate ligand is 8-hydroxyquinoline or 2-(o-hydroxyphenyl)-benzoxazole.

11. The compound of claim 2, wherein the bidentate ligand is 8-hydroxyquinoline or 2-(o-hydroxyphenyl)-benzoxazole.

* * * * *

UNITED STATES PATENT AND TRADEMARK OFFICE
CERTIFICATE OF CORRECTION

PATENT NO.   : 6,410,766 B2                                                                              Page 1 of 1
DATED        : June 25, 2002
INVENTOR(S)  : Yong Qiu and Yan Shao It is certified that error appears in the above-identified patent and that said Letters Patent is hereby corrected as shown below:

<u>Title page,</u>
Item [73], Assignee, "Tsinghau University" should read -- Tsinghua University --.

Signed and Sealed this

Twenty-second Day of April, 2003

JAMES E. ROGAN
*Director of the United States Patent and Trademark Office*